United States Patent [19]
Good et al.

[11] Patent Number: 6,058,933
[45] Date of Patent: May 9, 2000

[54] RESUSCITATOR BAG EXHAUST PORT WITH $CO_2$ INDICATOR

[75] Inventors: Robert J. Good, Raytown, Mo.; Joel Colburn, Hayward, Calif.

[73] Assignee: Nellcor Puritan Bennett Incorporated, Pleasanton, Calif.

[21] Appl. No.: 09/055,093

[22] Filed: Apr. 3, 1998

Related U.S. Application Data

[63] Continuation-in-part of application No. 08/729,618, Oct. 10, 1996, Pat. No. 5,749,358.
[51] Int. Cl.[7] .................................................. A62B 9/02
[52] U.S. Cl. .............................. 128/205.13; 128/205.24; 128/202.28; 128/205.28; 128/205.23
[58] Field of Search ................. 128/205.13, 205.23, 128/205.28, 202.28, 204.18, 205.27, 203.11, 205.24

[56] References Cited

U.S. PATENT DOCUMENTS

| | | | |
|---|---|---|---|
| 4,790,327 | 12/1988 | Despotis | 128/205.23 |
| 5,517,985 | 5/1996 | Kirk et al. | 128/205.28 |
| 5,749,358 | 5/1998 | Good et al. | 128/205.23 |

*Primary Examiner*—John G. Weiss
*Assistant Examiner*—V. Srivastava
*Attorney, Agent, or Firm*—Townsend and Townsend and Crew LLP

[57] ABSTRACT

A carbon dioxide indicator in an exhaust port of a resuscitator assembly. The carbon dioxide indicator is preferably in a removable insert for ease of maintenance and replacement. Breath-to-breath indications are provided by either exposing the indicator to the ambient air at the exhaust port, or diverting a portion of the fresh air or gases provided to the patient.

11 Claims, 6 Drawing Sheets

RESUSCITATOR BAG EXHAUST PORT WITH CO₂ INDICATOR

This application is a continuation-in-part of and claims the benefit of U.S. application Ser. No. 08/729,618, filed Oct. 10, 1996 now U.S. Pat. No. 5,749,358 the disclosure of which is incorporated by reference. This application is a continuation-in-part of application Ser. No. 08/729,618, filed Oct. 10, 1996, entitled RESUSCITATOR BAG EXHAUST PORT WITH CO₂ INDICATOR.

BACKGROUND OF THE INVENTION

The present invention relates to carbon dioxide indicators for use with a resuscitation bag.

The need for, and practice of, endotracheal intubation into the trachea of a patient is well-known. Such intubation is performed when it is found that normal ventilation of the patient's lungs may be impaired. Failure to artificially ventilate an apneic patient rapidly could result in serious brain damage or death.

In general, the endotracheal tube which is used to provide ventilation is a flexible tube which defines an internal respiration lumen so that once the tube has had its distal end placed within the trachea of the patient, a bidirectional breathing path is established through the respiratory lumen. In the case of interruption of the respiratory process, a resuscitator bag can be attached to the proximal end of the endotracheal tube, which end extends external to the patient.

One of the long recognized disadvantages of the use of an endotracheal tube is that an accidental misplacement of the tube into the esophagus can in itself cause death and disability if not quickly detected. In the prior art, a primary means of detecting accidental esophageal intubation has been utilizing a gaseous element detector connected within the air flow path of the respiring patient.

U.S. Pat. Nos. 4,728,499; 4,879,999; and 4,994,117 are examples of prior art devices which utilize a carbon dioxide detector to ensure proper placement of the endotracheal tube. The general concept of detecting the presence of carbon dioxide is a successful safety measure to detect esophageal intubation. Carbon dioxide, a product of metabolism, is normally present in exhaled air in approximately a 5% concentration, but is only minutely present in esophageal gas. Thus, if an approximately 5% concentration of carbon dioxide is detected in air exhaled from the endotracheal tube, the tube is not misplaced in the esophagus. In preferred embodiments of this safety device, a calorimetric carbon dioxide detector is used to enable the personnel responsible for placing the endotracheal tube to have a rapid visual indication of the presence of carbon dioxide.

A resuscitator bag may also be used with a mask placed over a patient's mouth and nose, with the carbon dioxide indicator revealing whether the patient is ventilating at all by exhaling carbon dioxide. Preferably, the indicator turns one color in the presence of carbon dioxide, and then turns back to another when the concentration drops due to the inspiratory breath given to the patient.

FIG. 1 illustrates a prior art resuscitator bag assembly 10 attached to an endotracheal tube 12 inserted into a patient's trachea 14. The assembly includes a resuscitator bag 16 having an inlet port 18 and an outlet port 20. A regulator 22 is attached to the outlet port 20 to provide gases or air from bag 16 through an elbow connector 24 to endotracheal tube 12. An exhaust port 26 connected to regulator 22 provides a path for exhaled gases to be exhausted. An indicator strip 28 is mounted in one end of the regulator 22 to provide an indication of carbon dioxide by changing color. Such a device is described in more detail in U.S. Pat. No. 5,279,289.

FIG. 2 is a cutaway view of one embodiment of a prior art regulator 20 of FIG. 1. When the resuscitator bag 16 is compressed, air or gas is forced along a path indicated by dotted line 30 through a slit at the peak of a duckbill valve 32 to the patient. The forced air or gas causes a gap 34 between the duckbill valve and a tubular lumen 36 to close, blocking off an escape path through exhaust port 26. When air is exhaled by the patient, it follows a path indicated by dotted lines 38 through the regulator, through openings 34 which are pressed open by pushing the duckbill valve 32 lower, and out exhaust port 26.

In this embodiment, the exhaust gases must pass through a barrier filter 40 to reach indicator 28. This can slow the response time of the carbon dioxide indicator. In addition, since the indicator is out of the direct flow path, it will not be cleared by a reduction in carbon dioxide concentration upon forced entry of air to a patient. This is because the carbon dioxide will be caught in the dead space by the indicator. While this is useful for indicating a single exhalation of a patient, it does not allow breath-to-breath determination. The lack of a breath-to-breath indication can give a false reading of proper intubation. In some instances carbon dioxide may be present in a patient's stomach sufficient to cause an initial indication, but not repeated indications. For instance, if a patient recently consumed a few sodas, there may be sufficient carbon dioxide to provide a false indication of proper intubation. Although the CO₂ would decrease over time in this case, the initial false indication would have serious clinical implications. A more detailed description of an apparatus as in FIG. 2 is set forth in U.S. Pat. No. 5,375,592.

U.S. Pat. No. 4,945,918 to Abernathy shows a carbon dioxide indicator strip in a closed-end chamber just beyond an exhaust port for a resuscitator system.

FIG. 3 is a diagram of a prior art carbon dioxide indicator which can be separately inserted into the line between a resuscitator bag and a patient, such as between elbow connector 24 and endotracheal tube 12 of FIG. 1. The assembly of FIG. 3 has a carbon dioxide indicator paper 42 which is viewable through a clear dome 44. Gases can pass through a porous filter 46 and through and around a baffle and indicator support 48. The disadvantage of such an indicator assembly is that it is another piece which must be assembled before treating the patient. At times, it may be time critical to quickly provide air to the patient, and such additional parts to assemble can be a disadvantage.

It would be desirable to have a carbon dioxide indicator which is part of the resuscitator assembly and is located so as to provide breath-to-breath indications.

SUMMARY OF THE INVENTION

The present invention provides a carbon dioxide indicator in an exhaust port of a resuscitator assembly. The carbon dioxide indicator is preferably in a removable insert for ease of maintenance and replacement. Breath-to-breath indications are provided by either exposing the indicator to the ambient air at the exhaust port, or diverting a portion of the fresh air or gases provided to the patient.

In one embodiment, the carbon dioxide indicator is on an indicator substrate secured in an insert installed into the Positive End Expiratory Pressure (PEEP) port of an exhaust port assembly. In an alternate embodiment, the carbon dioxide indicator is located in an inner portion of the exhaust port surrounding a tubular lumen providing the inlet gas flow.

An indicator cover can be provided in one embodiment to protect the indicator from ambient light and moisture before use. Such a cover is preferably an opaque, cylindrical tube having an outer portion for surrounding the PEEP port, and an inner portion for shielding the carbon dioxide indicator, while providing a through passage. The through passage allows the exhaust port to work even if a user forgets to remove the protector.

The present invention thus provides a carbon dioxide indicator which is integral with the resuscitator bag assembly, and requires no last minute assembly by a user. In addition, the carbon dioxide indicator provides breath-to-breath indication by being exposed without impediment to the gas flows. The indicator is also easily accessed for maintenance and replacement.

For further understanding of the nature and advantages of the invention, reference should be made to the following description taken in conjunction with accompanying drawings.

DETAILED DESCRIPTION OF THE PREFERRED EMBODIMENTS

Figure 1:
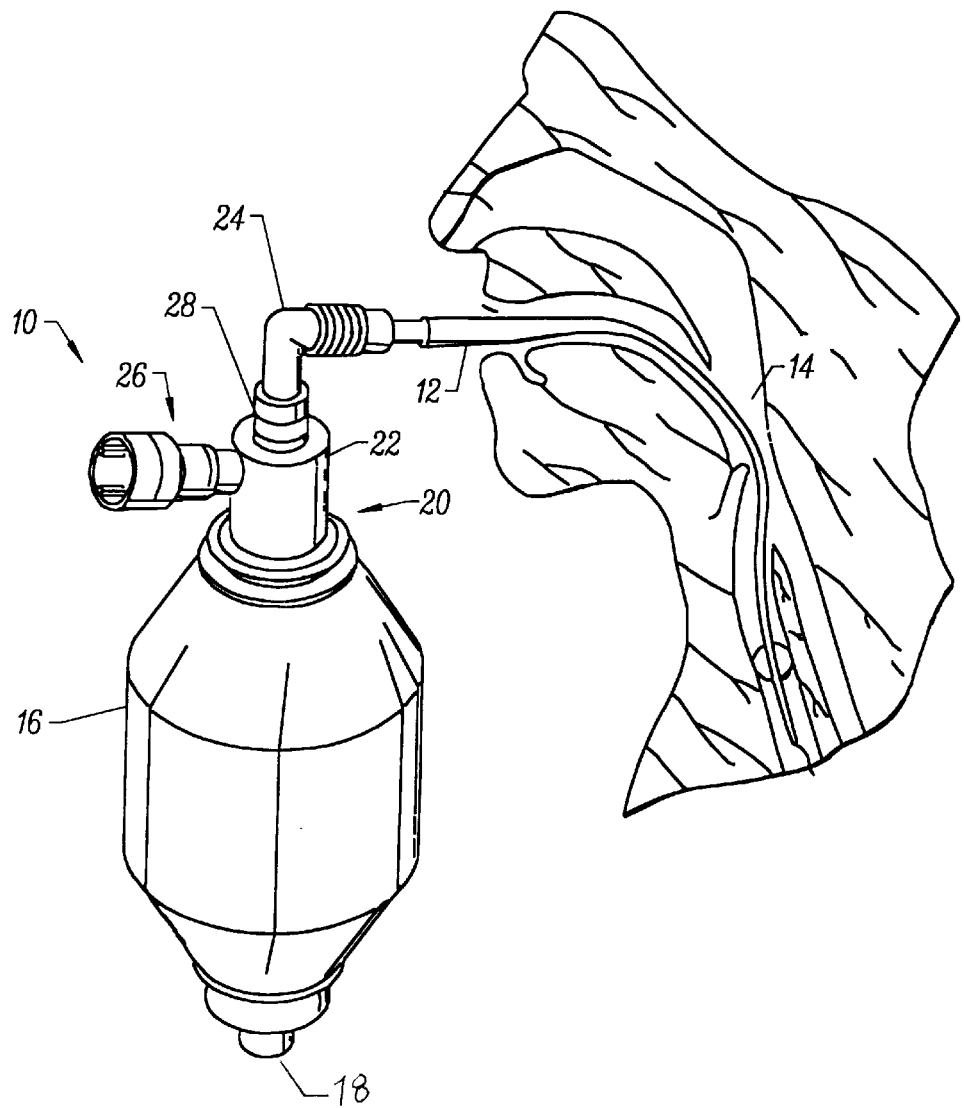
FIG. 1 is a perspective view of a resuscitator bag assembly connected to an endotracheal tube inserted into a patient according to the prior art.
Figure 2:
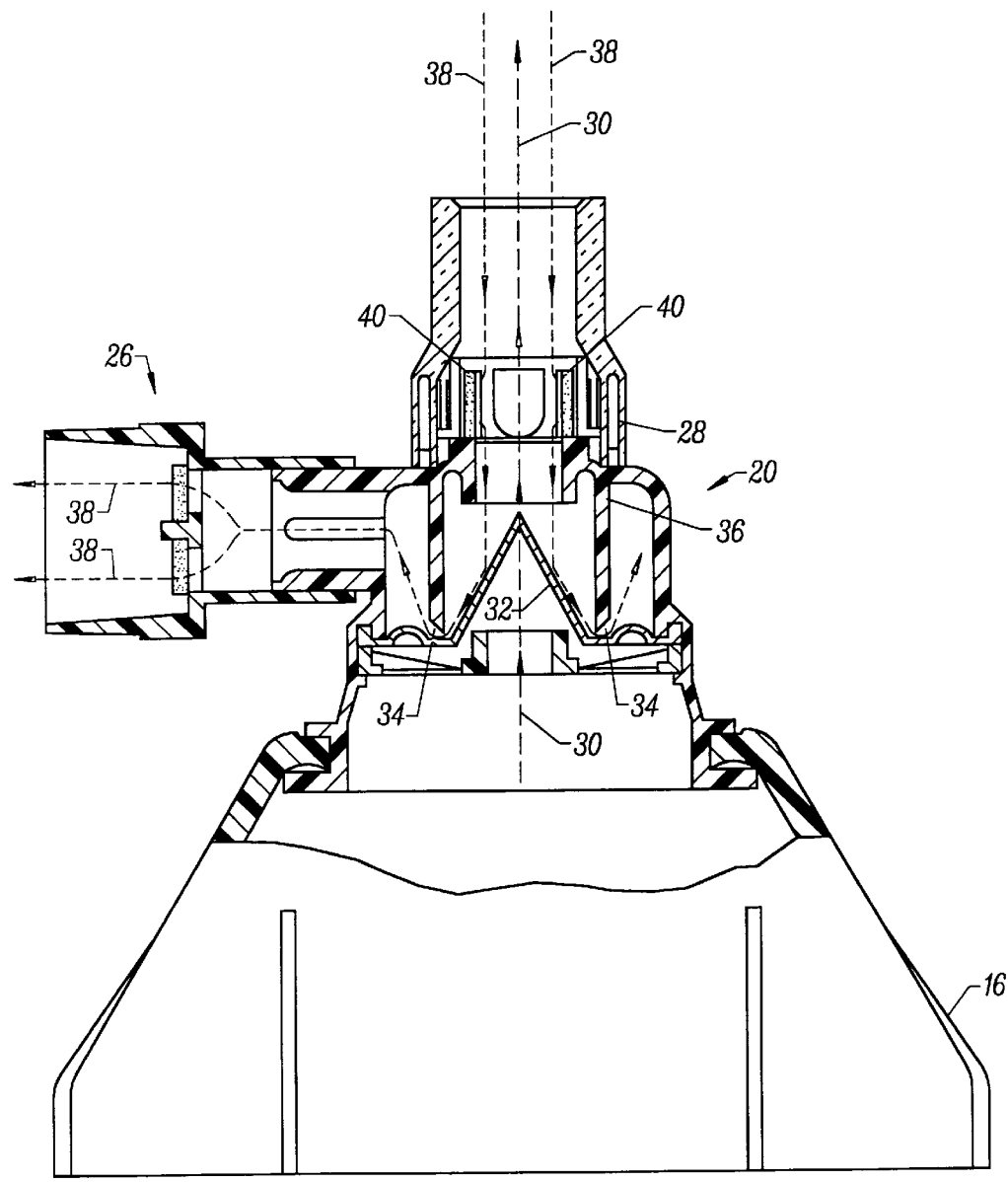
FIG. 2 is a cutaway, side view of a prior art regulator in the assembly of FIG. 1.
Figure 3:
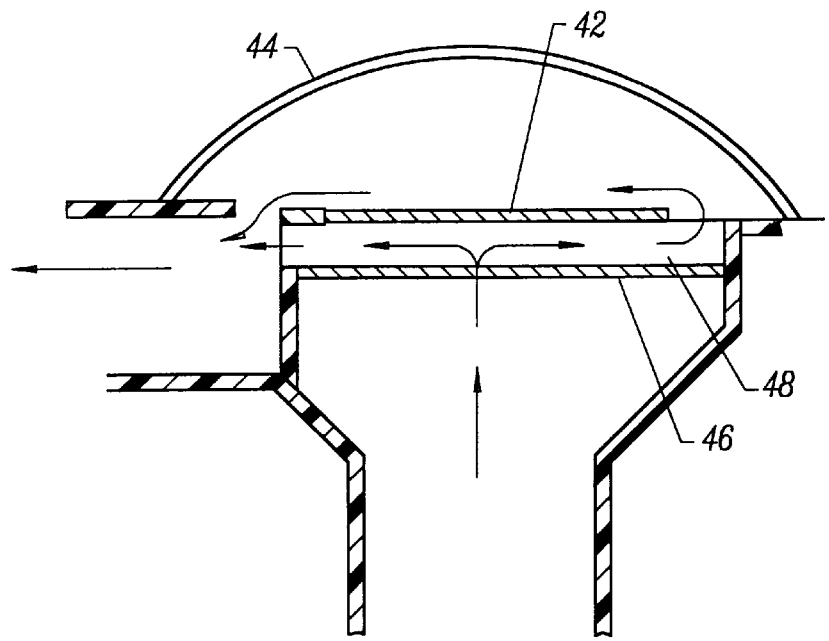
FIG. 3 is a cutaway, side view of a separate carbon dioxide indicator assembly according to the prior art.
Figure 4:
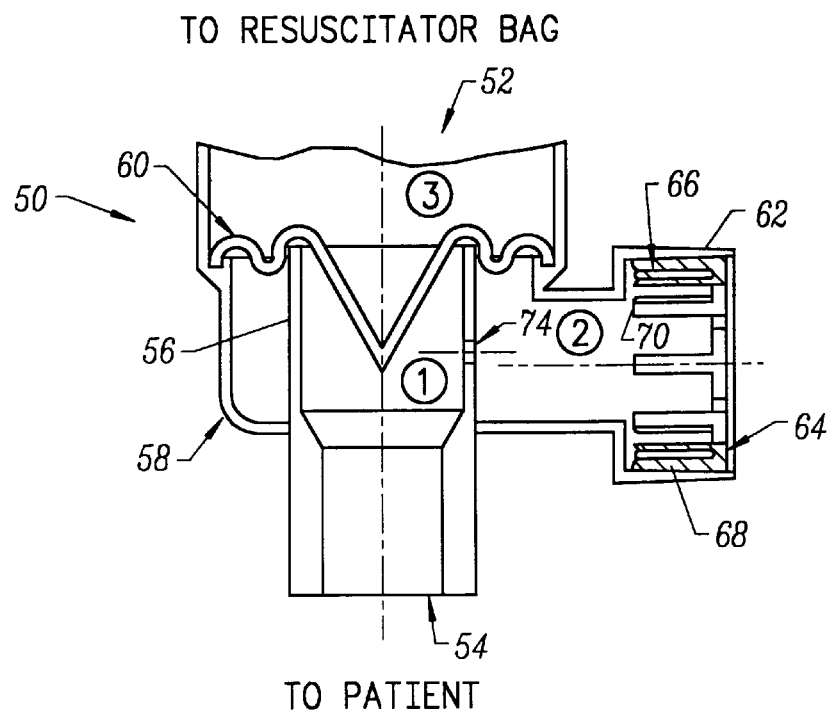
FIG. 4 is a cutaway, side view of a first embodiment of an exhaust port indicator according to the present invention.

FIG. 4 is a cutaway, sectional view of one embodiment of the present invention. A regulator assembly 50 has a port 52 for connecting to a resuscitator bag, and a port 54 for connecting to a patient. Port 54 includes a tubular lumen 56 which extends into an exhaust housing 58. A one-way valve 60 seals off exhaust assembly 58 when air is forced from the resuscitator bag through a slit in one-way valve 60 to the patient. When air is exhaled from the patient, valve 60 is pushed upward, allowing air to enter the exhaust port 58 and exit through an exterior portion of exhaust port 58. The exhaust port 58 optionally can be configured to accept a PEEP valve, and hence when so configured also constitutes a PEEP port 62 in addition to an exhaust port 58.

An insert assembly 64 is press-fitted into PEEP port 62, and holds a carbon dioxide indicator 66. Indicator 66 could be a chemical on a substrate of paper, porous polypropylene weave, nylon, etc. The indicator is wedged between the cylindrical wall 68 of insert 64, and slightly interior retaining members 70.

An optional hole 74 is shown in lumen 56. This allows some of the inlet gases from the resuscitator bag to enter the exhaust port on inhalation (or forced air entry). Otherwise, this exhaust port would be sealed off from the resuscitator bag during inhalation. This leaked amount of air allows the indicator 62 to be cleared, in the event that ambient air entering into the exhaust port is not sufficient. The indicator used will begin to turn from a first color (i.e., purple, green) to a series or graduation of second colors (i.e., ultimately yellow) upon detecting an initial $CO_2$ concentration greater than some predetermined amount, e.g., <0.5%, and turn back to the first color upon detecting a concentration at ambient air $CO_2$ concentrations (e.g., 0.03%), thus providing the breath-to-breath indication desired. A yellow color distinct from purple is preferably discernable upon detecting significant $CO_2$ concentrations, i.e., 1%, 2%, 3%, 4%, or 5%, depending on desired product performance. Preferably, hole 74 is of a size to allow less than 50%, more preferably less than 15% of the air or gases from the resuscitator bag 52 to escape, and more preferably approximately 10%.

Figure 5B:
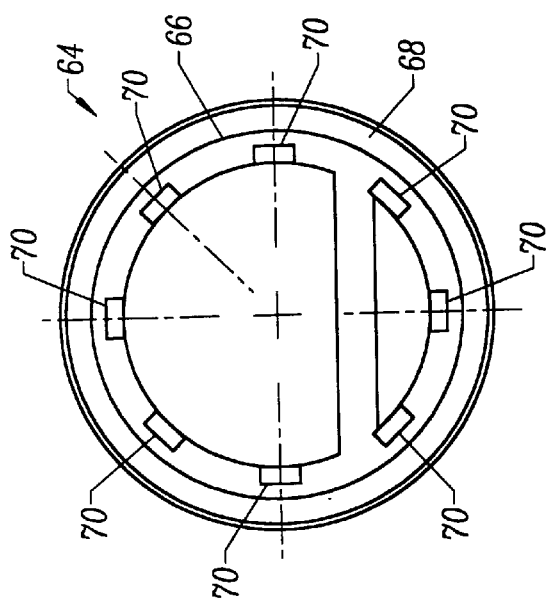
FIGS. 5A and 5B are side and top views of the indicator insert assembly of FIG. 4.
Figure 5A:
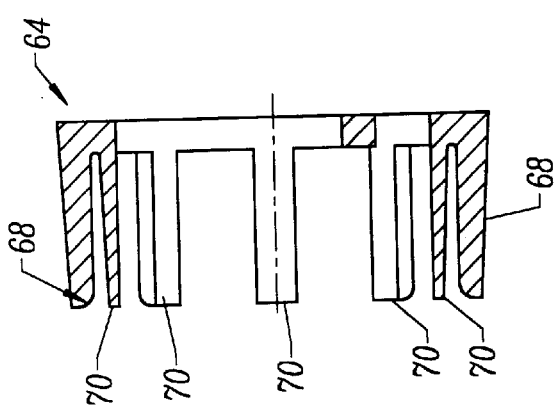

FIGS. 5A and 5B illustrate side and front views, respectively, of insert 64 of FIG. 4. These views show more clearly how the indicator 66, which can be cylindrical, is inserted into the ring-shaped enclosure between members 70 and the outer cylindrical wall 68 of the insert assembly. The outer wall 68 is at least partially transparent, allowing the indicator to be viewed through the walls of PEEP port 62, which are also preferably transparent. As can be seen from FIG. 4, the exterior wall 68 of insert 64 is preferably tapered, to allow a pressed fit into PEEP port 62. In one embodiment, insert 64 is made of a flexible plastic material, so that it can bend as it is press-fitted into the PEEP port 62.

Referring to FIG. 4, the outside diameter of PEEP port 62 is tapered and is of such a diameter such that it can accommodate a standard PEEP valve.

Figure 6:
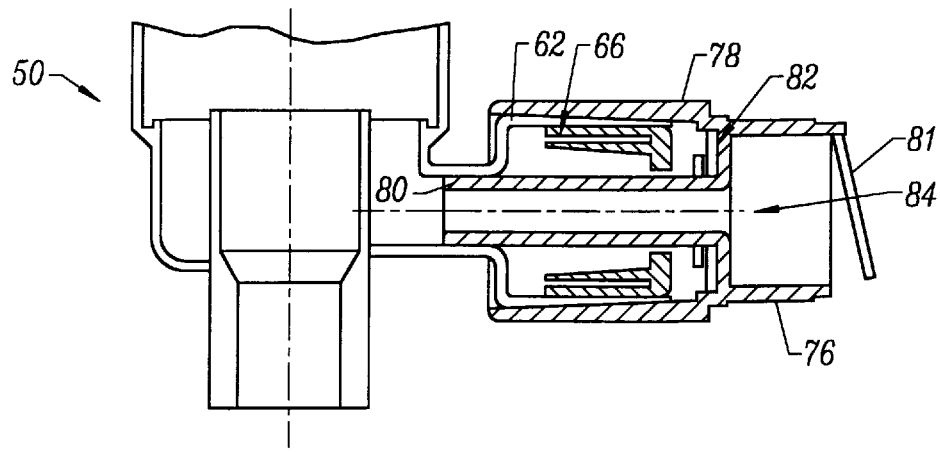
FIG. 6 is a diagram illustrating an indicator sealer according to one embodiment of the present invention.

FIG. 6 is a cutaway, sectional view of the regulator assembly 50 of FIG. 4 with a sealer 76 attached. The sealer has an outer, cylindrical portion 78 which attaches to the outside of the PEEP port 62. Sealer 76 is opaque, to prevent ambient light from affecting the $CO_2$ indicator 66 prior to usage. An inner, tubular portion 80 of sealer 76 seals the inside of the PEEP port. This prevents not only light from contacting the indicator 66 from the inside, but also moisture from reaching the indicator 66 by forming a seal against the walls of the PEEP port. The sealer may also include a desiccant 82 for absorbing moisture and further preventing moisture from affecting indicator 66.

Sealer 76 defines a through passage 84, allowing the resuscitator assembly to work even with the sealer 76 attached. This is important in the event that personnel using the resuscitator bag assembly forget to take off the sealer. At the same time, the sealer blocks the $CO_2$ indicator, encouraging a user to notice that the indicator is not visible, and thus remove the sealer to make it visible. The sealer may be made of a black plastic, such as Santoprene. Alternately, other sealers could be used, such as foil or paper. To ensure that a user removes the sealer, a separate sealer could be attached to the portion for connecting to the patient, with a string in between them to remind the user that both need to be removed.

In an alternate embodiment, a flapper or one-way valve 81 may be attached to the exhaust port. This valve would allow air to be exhausted, but would prevent air from being drawn in through the exhaust port. Valve 81 could be placed inside the exhaust port, so that it would not interfere with the sealer 76. Alternately, sealer 76 could be omitted, and instead the entire regulator assembly 50 could be sealed within an airtight bag, with a desiccant included within the bag to protect the carbon dioxide indicator. Such a bag could be tinted to prevent ambient light from affecting the indicator, if necessary.

Figure 7:
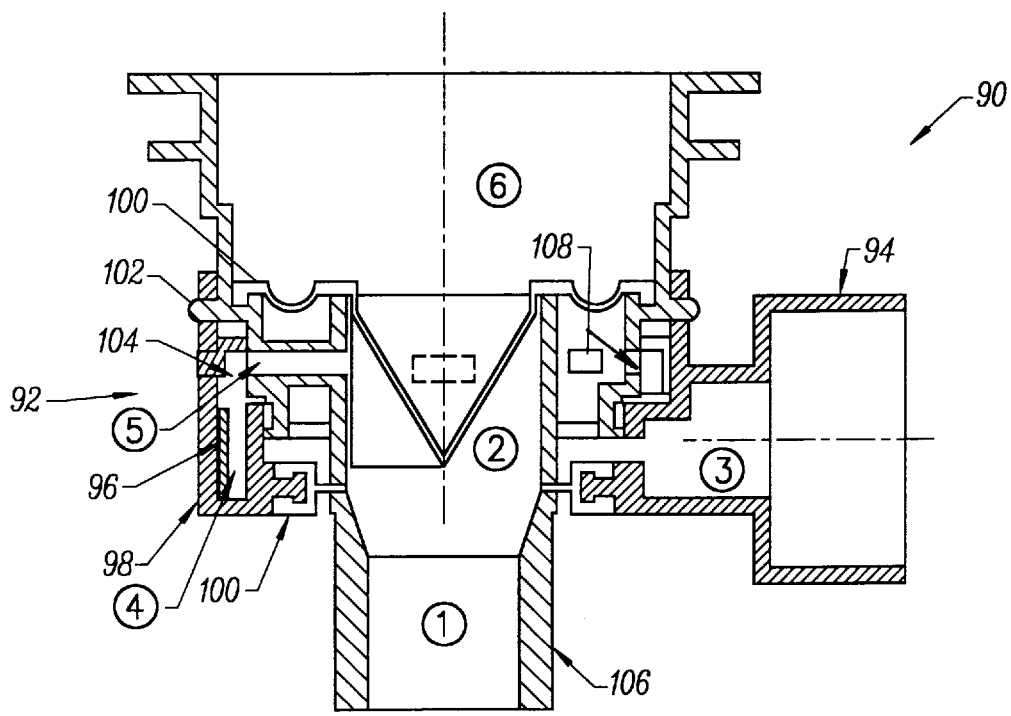
FIG. 7 is a cutaway, side view of an alternate embodiment of the present invention with the indicator in an inner portion of the exhaust port.

FIG. 7 is a cutaway, sectional view of an alternate embodiment of the present invention. A regulator assembly 90 is shown, with an exhaust port housing 92 and an attached PEEP port 94. In this embodiment, the indicator 96 is a partially circular strip inserted into the edges of exhaust port 92. In a particular embodiment shown, indicator 96 is adjacent the PEEP adapter housing wall 98.

In operation, a patient exhales into chamber 1. A one-way valve diaphragm 100 lifts and the exhaled gas goes into chambers 2, 3 and 4. Some gas will go through port 5 into chamber 4. Exhaled gas which goes into chamber 4 will turn the carbon dioxide indicator 96 to, e.g., yellow from purple.

In an inhalation mode, a resuscitator bag containing oxygen, room air or other gases will go from chamber 6 into chamber 1 and into the patient. Some air or oxygen from 6 will also go into port 5 and into the chamber 4. Exhaled gases will be pushed out of chamber 4. From chamber 4, the exhaled gases will go into chamber 2 then into chamber 3 and out into the atmosphere. The carbon dioxide indicator will turn from yellow to purple after the exhaled gas has been removed.

The PEEP adapter 98 can be turned by rotating it on guide pins 102. Holes in a switch seal 104 will move away from holes in an NRV housing 106. Thus, the seal will cover all the holes in NRV housing including port 5. In this position, the carbon dioxide indicator will be isolated from the environment in an "off" position, keeping the indicator from being degraded prior to use. Turning the PEEP adapter the opposite direction on the guide pins will align the holes and the switch seal with the holes and NRV housing 106. This allows the atmosphere into the carbon dioxide indicator for an "on" position.

By turning the PEEP adapter to align a slot on the PEEP adapter with the guide pins on the NRV housing 106, the PEEP adapter can be pulled off the NRV housing. With the same alignment positions, the PEEP adapter can be pushed back onto the NRV housing, as is known in the prior art.

Also illustrated in FIG. 7 are exhalation holes 108 connecting to the carbon dioxide indicator, and a rubber seal 110.

Figure 8:
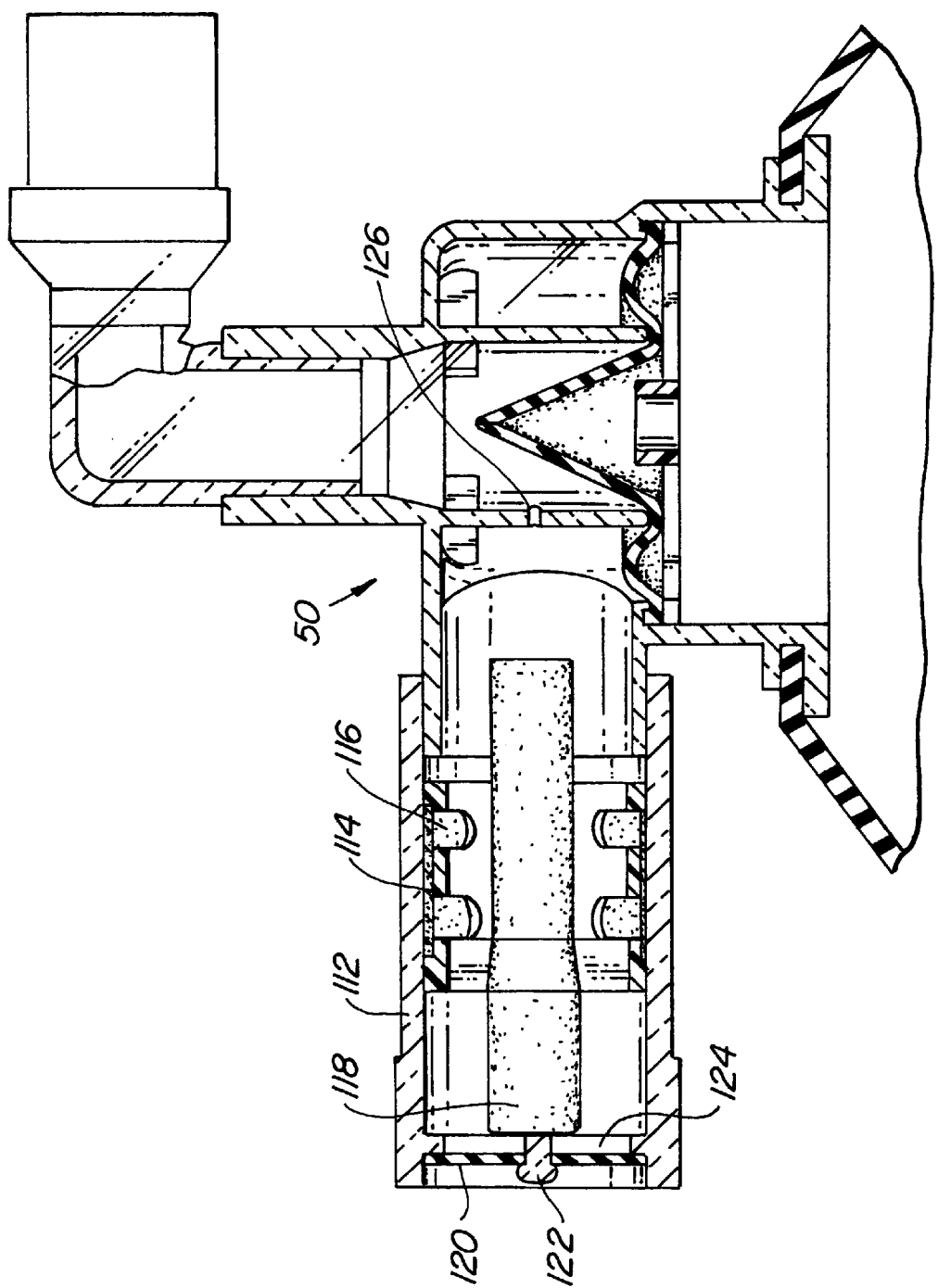
FIG. 8 is a diagram illustrating an alternate embodiment of a PEEP port with a flapper.

FIG. 8 illustrates an alternate embodiment of the invention which can be used with a sealed bag around the entire apparatus for performing the sealing function to protect the indicator. In this embodiment, a PEEP port 112 is attached to regulator assembly 50. No sealer, such as shown in FIG. 6, is included, since the entire PEEP port regulator assembly can be enclosed in a sealed bag to accomplish the same purpose. The indicator 114 is held along the inside edges of the PEEP port by a spool frame 116. A desiccant 118 is also included in the PEEP port.

A check valve 120 allows air to be expelled, but not drawn in through the PEEP port. Check valve 120 is a flexible flap mounted only at its center on a knob 122 which is part of a frame 124 in the exhaust port of the PEEP port. Frame 124 is preferably an X-shaped frame allowing the passage of air, but providing a seat for valve 120.

Desiccant 118 is center-mounted to allow an unimpeded flow of air around it through the exhaust port. By having the indicator paper 114 around the periphery of the exhaust port, a path for unimpeded air flow is provided between the desiccant and the indicator paper. The portion of the PEEP port 112 housing adjacent indicator 114 is transparent to allow ready viewing of the indicator paper. Alternately, the indicator paper could be mounted on an internal frame, or around the desiccant, while still being viewable from the outside through the transparent walls of the PEEP port, and also allowing unimpeded paths for the flow of gas.

The indicator 114 can provide a breath-to-breath indication, by changing color when $CO_2$ is provided from the patient, and then being cleared by oxygen from the resuscitator bag going through the exhaust port through a diverting passageway or clearing hole 126. Inhalation through the clearing hole during a patient breath from the exhaust port is prevented by valve 120.

Desiccant 118 is center-mounted to conveniently protect the indicator strip during shipment and storage of the device. The desiccant allows moisture to be absorbed during packaging, shipment and storage prior to use. By permanently affixing it inside the exhaust port (or PEEP port), the user is not required to remove it prior to use. This allows quick opening and application of the resuscitator device in an emergency situation without requiring the user to remove the desiccant, while at the same time providing an effective placement of the desiccant near the $CO_2$ indicator paper.

As will be understood by those with skill in the art, the present invention may be embodied in other specific forms without departing from the spirit or essential characteristics thereof. For example, the desiccant could be mounted in the indicator insert housing, rather than attached to the sealer. Accordingly, the foregoing description of the preferred embodiments is intended to be illustrative, but not limiting, of the scope of the invention which is set forth in the following claims.

What is claimed is:

1. A resuscitator device for supplying gas to a patient, comprising:

a regulator providing a main passageway to said patient;

an exhaust housing in fluid communication with said regulator, said housing having an exhaust port end and a regulator end, said regulator end adjacent said regulator, said exhaust port exhausting into ambient air, said exhaust port including at least a portion which is transparent; and a carbon dioxide indicator mounted in said exhaust port at a position viewable through said transparent portion where said indicator leaves an unimpeded pathway for gas through said exhaust port.

2. The device of claim 1 wherein said exhaust port includes a PEEP port, said carbon dioxide indicator being mounted in said PEEP port.

3. The device of claim 1 wherein said carbon dioxide indicator is embedded on paper.

4. The device of claim 1 wherein said regulator is configured to isolate said exhaust port from fresh gases from said regulator, and further comprising a diverting passageway between said regulator and said exhaust port to divert a fraction of said fresh gases to said exhaust port to clear said carbon dioxide indicator.

5. The device of claim 4 wherein said fraction of fresh gases diverted is 50% or less.

6. The device of claim 4 wherein said diverting passageway comprises a hole in a wall of said main passageway.

7. The device of claim 1 further comprising a one-way valve mounted in said exhaust port.

8. The device of claim 7 wherein said one-way valve comprises a flexible flap fastened to the center of a frame mounted in said exhaust port.

9. The device of claim 1 further comprising a cylindrical desiccant mounted along a center axis of said exhaust housing.

10. The device of claim 1 wherein said exhaust housing comprises a PEEP port.

11. A method for providing a breath-to-breath indication of carbon dioxide detection in a resuscitator, comprising the steps of:

provQuantum a regulator, and an exhaust port housing in fluid communication with said regulator, said housing having an exhaust port end and a regulator end, said regulator end adjacent said regulator, said exhaust port exhausting into ambient air;

inserting a carbon dioxide indicator into said exhaust port where said indicator leaves an unimpeded pathway for gas through said exhaust port; and sealing said carbon dioxide indicator from ambient light and moisture.

\* \* \* \* \*